US009919119B2

United States Patent
Sovndal

(10) Patent No.: US 9,919,119 B2
(45) Date of Patent: Mar. 20, 2018

(54) GUM ELASTIC BOUGIE INTRODUCER WITH TACTILE DEPTH AND ORIENTATION INDICATOR

(71) Applicant: Shannon Sovndal, Louisville, CO (US)

(72) Inventor: Shannon Sovndal, Louisville, CO (US)

( * ) Notice: Subject to any disclaimer, the term of this patent is extended or adjusted under 35 U.S.C. 154(b) by 694 days.

(21) Appl. No.: 13/956,202

(22) Filed: Jul. 31, 2013

(65) Prior Publication Data

US 2015/0034078 A1 Feb. 5, 2015

(51) Int. Cl.
*A61M 16/04* (2006.01)
*A61M 25/01* (2006.01)

(52) U.S. Cl.
CPC ..... *A61M 16/0488* (2013.01); *A61M 16/0465* (2013.01); *A61M 2205/0222* (2013.01); *A61M 2205/0266* (2013.01); *A61M 2205/582* (2013.01); *A61M 2205/584* (2013.01)

(58) Field of Classification Search
CPC ...... A61M 16/00; A61M 16/04; A61M 27/00; A61M 31/00; A61M 39/00; A61M 16/0488; A61M 16/0493; A61M 16/0497; A61M 2205/0222; A61M 2205/582; A61M 16/0429; A61M 16/0431; A61M 2210/1028; A61M 2210/1032; A61M 2210/1035; A61M 2210/0618; A61M 25/0102; A61M 25/01; A61B 17/8811
USPC ................... D24/133, 141; 33/492; 604/264
See application file for complete search history.

(56) References Cited

U.S. PATENT DOCUMENTS

| 4,185,639 | A |   | 1/1980 | Linder |
|---|---|---|---|---|
| 4,825,858 | A | * | 5/1989 | Frankel ............ A61M 16/0488 128/200.26 |
| 5,042,475 | A | * | 8/1991 | LaBombard ...... A61M 16/0429 128/200.26 |
| 5,366,471 | A |   | 11/1994 | Jones et al. |
| 5,718,666 | A |   | 2/1998 | Alarcon |
| 5,766,202 | A |   | 6/1998 | Jones et al. |
| 5,919,183 | A |   | 7/1999 | Field |
| 6,718,970 | B2 |   | 4/2004 | Sniadach |
| 6,740,082 | B2 |   | 5/2004 | Shadduck |
| 7,309,344 | B2 |   | 12/2007 | Bakos et al. |
| 7,650,886 | B1 | * | 1/2010 | Keller ............... A61M 16/0488 128/207.14 |

(Continued)

FOREIGN PATENT DOCUMENTS

| EP | 0138089 B1 | 4/1985 |
|---|---|---|
| ES | 2283187 A1 | 10/2007 |

(Continued)

OTHER PUBLICATIONS

Airway Cam Technologies, Inc., "Bougie (Tube Introducer)", Webpage found at http://www.airwaycam.com/tube-introducers.html downloaded on Mar. 20, 2013, 2011, p. 2, Published in: US.

(Continued)

*Primary Examiner* — Peter S Vasat
(74) *Attorney, Agent, or Firm* — Neugeboren O'Dowd PC

(57) ABSTRACT

This disclosure describes systems, methods, and apparatus for intubation where indicators of a bougie's axial orientation and insertion depth into the trachea are not visible. In particular, a bougie having one or more tactile indicators of axial orientation and/or depth of insertion are disclosed. The tactile indicators can include finger grooves and/or a ridge to name two examples.

21 Claims, 6 Drawing Sheets

(56) References Cited

U.S. PATENT DOCUMENTS

| | | | |
|---|---|---|---|
| 8,161,967 B2 | 4/2012 | Harms et al. | |
| 2007/0175482 A1* | 8/2007 | Kimmel | A61B 1/018 128/207.14 |
| 2008/0017195 A1 | 1/2008 | Yoshida | |
| 2008/0230056 A1 | 9/2008 | Boedecker | |
| 2009/0306472 A1 | 12/2009 | Filipi et al. | |
| 2010/0179511 A1* | 7/2010 | Rajan | A61M 11/00 604/514 |

FOREIGN PATENT DOCUMENTS

| | | |
|---|---|---|
| WO | 2002009799 A1 | 2/2002 |
| WO | 2007093786 A1 | 8/2007 |

OTHER PUBLICATIONS

Sime, et al., "The Bougie: An Inexpensive Lifesaving Airway Device", "The Journal of Emergency Medicine", 2012, pp. e393-e395, vol. 43, No. 6, Publisher: Elsevier Inc., Published in: US.

Combes, et al., "Emergency gum elastic bougie-assisted tracheal intubation in four patients with upper airway distortion", Jan. 14, 2004, p. 3 Publisher: Société Française d'Anesthésie et de Réanimation***, Published in: FR.

SP Services Ltd, "Eschmann Tracheal Tube—Introducer 15CH×60CM", Webpage found at www.spservices.co.uk/item/Brand_EschmannTrachealTube-Introducer15Chx60cm_57_0_2516_0.html downloaded on Jul. 19, 2013, 2013, p. 2 Published in: GB.

Salem MR, "Verification of endotracheal tube position.", Webpage found at www.ncbi.nlm.nih.gov/pubmed/11778382 downloaded on Jul. 19, 2013, Dec. 19, 2001, p. 2 Publisher: Department of Anesthesiology, Advocate Illinois Masonic Medical Center, Published in: US.

Weisenburg, et al., "Endotracheal Intubation with a Gum-Elastic Bougie in Unanticipated Difficult Direct Laryngoscopy: Comparison of a Blind Technique Versus Indirect Laryngoscopy with a Laryngeal Mirror", Webpage found at www.anesthesia-analgesia.org/content/95/4/1090.full downloaded on Jul. 18, 2013, Oct. 2002, p. 5 Publisher: Anesthesia & Analgesia, Published in: US.

* cited by examiner

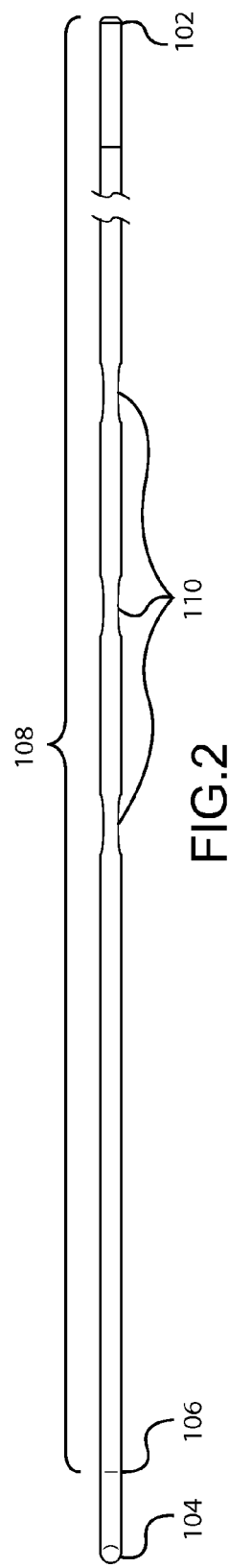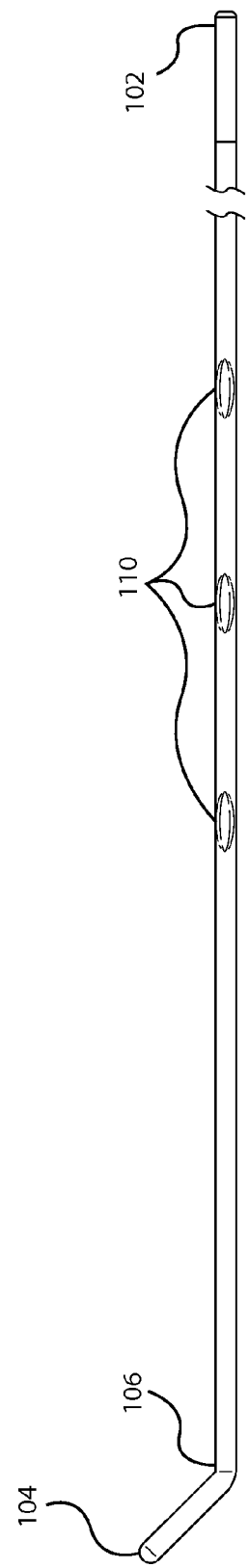

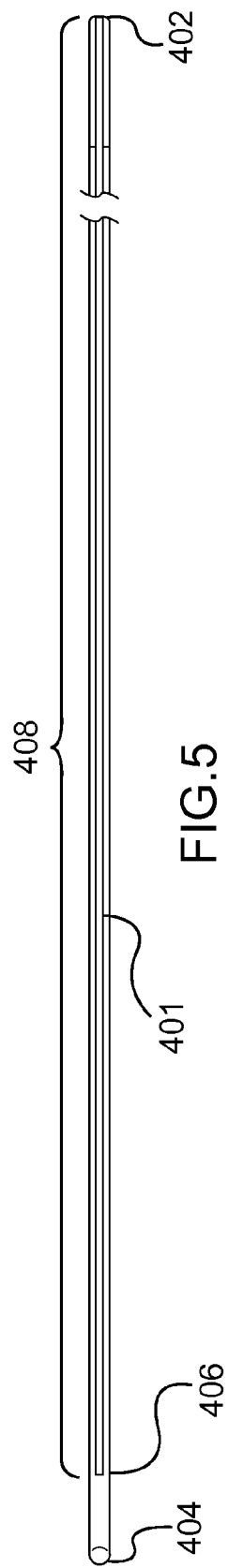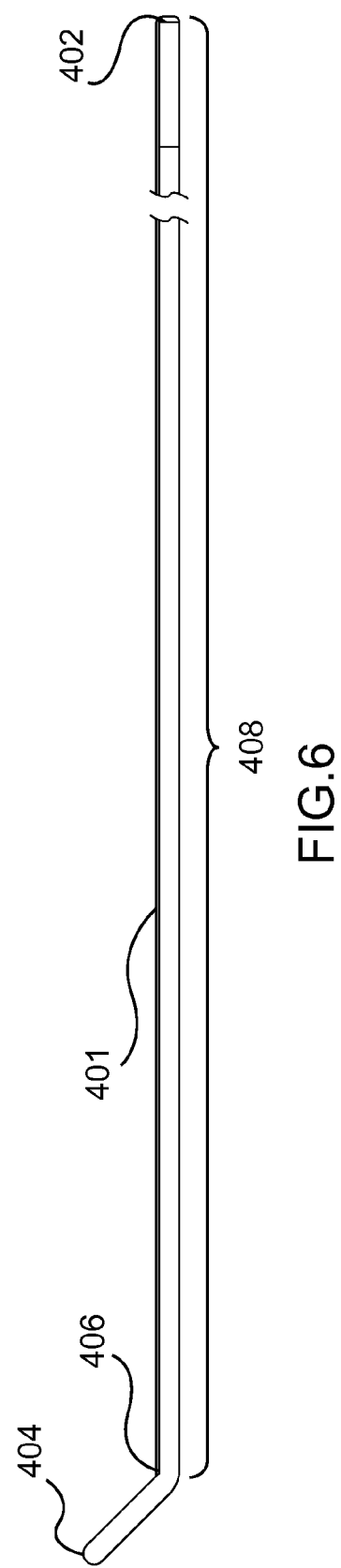

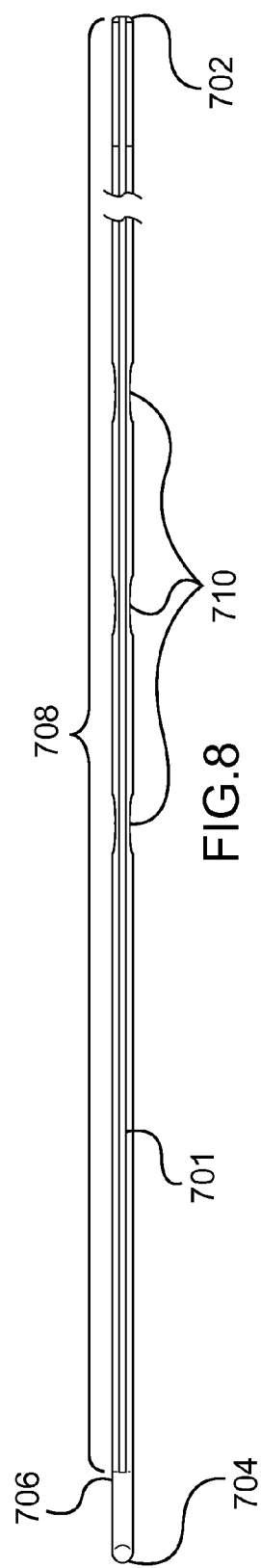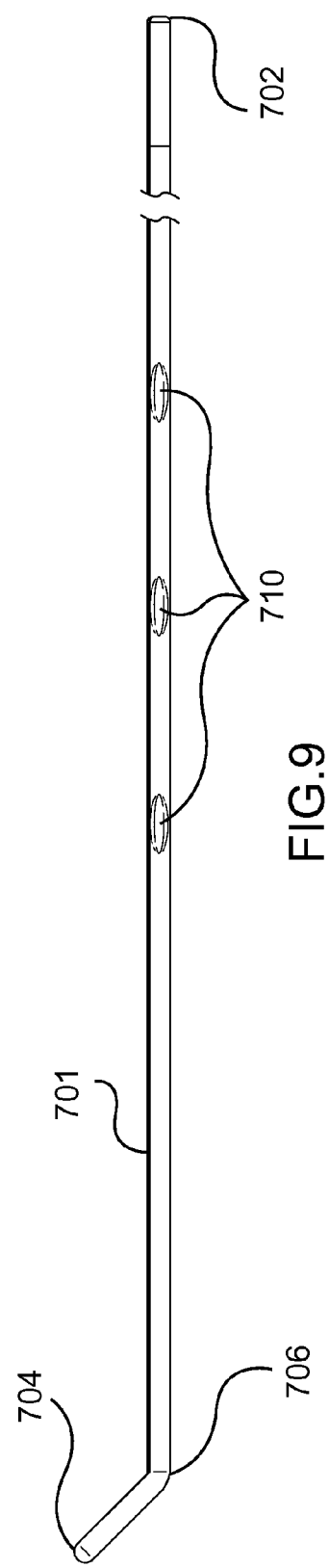

GUM ELASTIC BOUGIE INTRODUCER WITH TACTILE DEPTH AND ORIENTATION INDICATOR

FIELD OF THE DISCLOSURE

The present disclosure relates generally to medical devices. In particular, but not by way of limitation, the present disclosure relates to systems, methods and apparatuses for a gum elastic bougie.

BACKGROUND

The gum elastic bougie, bougie introducer, tube introducer, or endotracheal tube introducer (hereinafter "bougie") is a narrow diameter tracheal device that is the preferred adjunct device for intubation. It is critical and life saving that the introducer and endotracheal tube be introduced into the trachea rather than the esophagus. Although newer fiber optics and video laryngoscopes are available, their expense, complexity, lack of availability in every situation, and utility of the bougie means that the bougie is still widely used. In fact, the bougie is still used in conjunction with these newer devices. The bougie is often utilized where patients have anterior airways, airways obscured by blood or secretions, or limited neck mobility.

The bougie has a distal tip or coude tip that bends (e.g., at an angle of 35-40°) so as to assist the user in moving the distal tip into the trachea (or air passage) rather than down the esophagus. Since the trachea sits anterior to the esophagus, the device, if not carefully maneuvered, is more likely to enter the esophagus than the trachea. Ideally, positioning techniques can be used so that an emergency expert can visulize the glottic opening, or at least a part of the trachea, and guide the distal tip into the trachea. However, in some cases the glottic opening may not be visible or the angle too great to position the endotracheal tube. For instance, this may occur where the head cannot be tilted back, the patient has abnormal anatomy, the patient is pediatric age or there is obscuring blood and secretions. In such instances, bougie users must rely on feel and experience alone to guide the distal tip into the correct passage.

This procedure requires that proper depth of insertion and axial orientation of the distal tip be achieved. Depth should be sufficient for the distal tip to pass the vocal chords. Depth is typically gauged by measuring the bougie against the external anatomy of the patient and noting the needed depth. Once placed in the oropharanx, the operator also gauges depth by feeling "tracheal clicks" as the distal tip moves over ribs in the trachea. Since these ribs are only on an anterior 180° of the trachea, it is essential to keep the distal tip of the bougie pointed toward an anterior 180° of the trachea. However, every patient's anatomy is different and thus 'feeling' the orientation of the distal tip can be challenging and inconsistent. Alternatively, bougies occasionally have been produced with one or more visual depth indicators printed on them to assist in achieving proper depth of insertion. However, these indicators become difficult if not impossible to see in circumstances where liquids (e.g., blood) are present or where lighting is poor.

Furthermore, successfully passing the distal tip through the glottic opening as opposed to the esophagus is far more likely when the distal tip is bent toward or facing an anterior of the neck. Yet, once in the airway the distal tip is not visible, and because the shape is tubular and smooth there is little or no indication of the distal tips's orientation. Users are often forced to attempt to 'feel' the distal tip's orientation as it contacts known parts of the throat and trachea.

These inherent flaws in the traditional bougie, which can be life threatening, have been well known to users of the bougie for decades. Yet, the product has remained largely unchanged and without significant innovation in this regard. Medical textbooks do not discuss these challenges, and leadership in the medical field has further ignored these problems thus leaving it to bougie users to deal with these challenges in ways that are not ideal and that have endangered lives for many years.

SUMMARY OF THE DISCLOSURE

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

Some embodiments of the disclosure may be characterized as a bougie including a flexible elongated distal portion, and a flexible elongated main portion. The flexible elongated main portion can be coupled to the distal portion at an angle and can be longer than the distal portion. The angle can be oriented toward a superior side of the main portion. The main portion can include one or more pairs of finger grooves, each pair including a finger groove on a left side and on a right side of the main portion. The finger grooves can provide a tactile indication of an axial orientation of the bougie as well as a tactile indication of a depth of insertion of the bougie into a trachea. The finger grooves can further provide an improved grip when the bougie becomes slippery due to blood, secretions, or other liquids.

Other embodiments of the disclosure may also be characterized as a bougie including a flexible elongated distal portion and a flexible elongated main portion. The flexible elongated main portion can include one or more tactile indicators of an axial orientation of the bougie and a depth of insertion of the bougie into the trachea. Further, the one or more tactile indicators can be recognizable to human touch even when obscured to view by patient bodily fluids. Additionally, the finger grooves can further provide an improved grip when the bougie becomes slippery due to blood, secretions, or other liquids Other embodiments of the disclosure can be characterized as a method for using a bougie. The method can include providing a bougie having an elongate shape, a bent distal tip, and one or more tactile indicators of an orientation of the bent distal tip and a depth of insertion of the bougie. The one or more tactile indicators can provide an improved grip when the bougie becomes slippery due to blood, secretions, or other liquids. The method can further include rotating the bougie until the one or more tactile indicators indicates that the distal tip of the bougie is pointed toward an anterior side of the trachea. Finally, the method can include moving the bougie into a patient until the one or more tactile indicators indicates that the bougie has entered the trachea.

BRIEF DESCRIPTION OF THE DRAWINGS

Various objects and advantages and a more complete understanding of the present invention are apparent

FIG. 2 illustrates an overhead view of a bougie according to the one embodiment of this disclosure;

FIG. 3 illustrates a side view of a bougie according to the one embodiment of this disclosure;

FIG. 5 illustrates an overhead view of a bougie according to the another embodiment of this disclosure;

FIG. 6 illustrates a side view of a bougie according to the another embodiment of this disclosure;

FIG. 8 illustrates an overhead view of a bougie according to the yet another embodiment of this disclosure; and FIG. 9 illustrates a side view of a bougie according to the yet another embodiment of this disclosure.

DETAILED DESCRIPTION

The word "exemplary" is used herein to mean "serving as an example, instance, or illustration." Any embodiment described herein as "exemplary" is not necessarily to be construed as preferred or advantageous over other embodiments.

For the purposes of this disclosure, a "bougie" is any device used as a guide to aid insertion of other medical appliances via the oral cavity or other potential anatomical space. Typically the bougie is removed once the other medical appliance is in place.

For the purposes of this disclosure, an "axial orientation" of the bougie describes an orientation of the bougie relative to an axis passing through the longest dimension of the bougie (e.g., its length).

Finger grooves and/or a ridge along a superior portion of a bougie are herein disclosed, thus overcoming the long-felt unsolved needs discussed above, by enabling a user to know a depth and axial orientation of the bougie via touch rather than sight, even if the device is covered in secretions, blood, lubricants or fluids.

Figure 1:
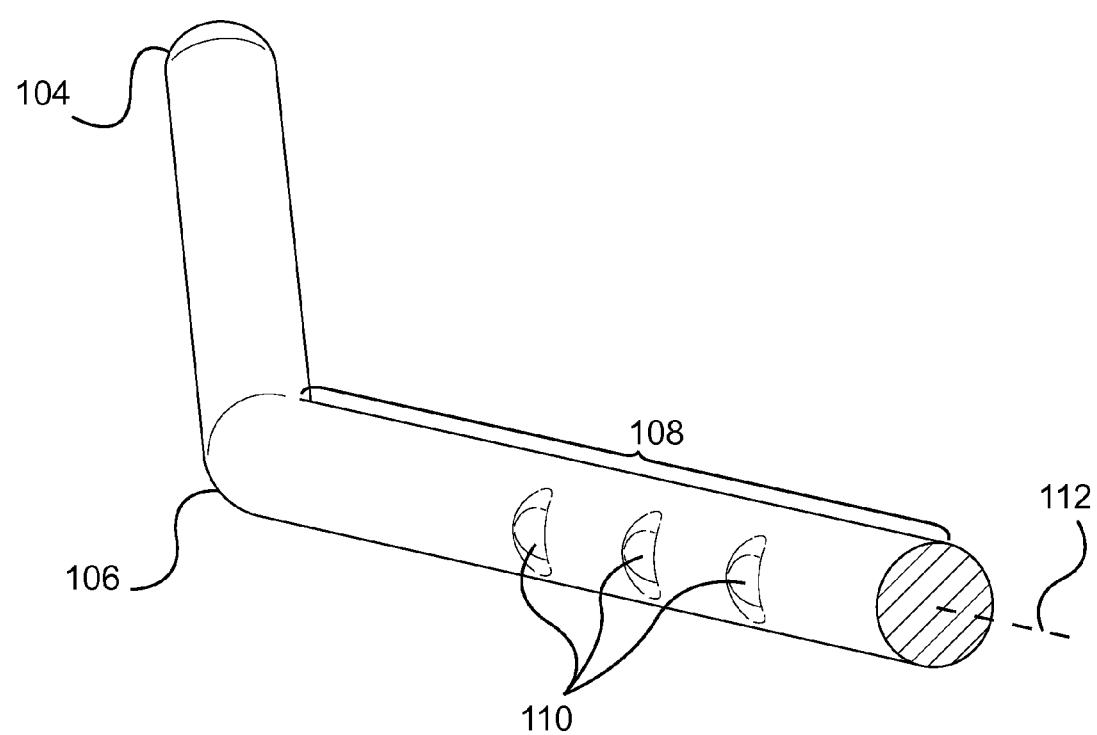
FIG. 1 illustrates a perspective view of a bougie according to one embodiment of this disclosure.

FIGS. 1-3 illustrate a bougie according to one embodiment of this disclosure. The bougie comprises an elongate body having a proximal end 102 and a distal tip 104. The distal tip 104 can include a bend 106 that may be deflected or bent from a main portion 108 of the bougie by an angle such as 38°. The proximal end 102 is cutoff in FIG. 1 due to the length of the main portion 108 and difficulty of showing the bougie to scale if the full main portion 108 were displayed. Similarly, FIGS. 2 and 3 show the proximal end 102, but only a portion of the main portion 108, as scale would make the illustrated bougie longer than the span of the figures allows.

The bougie can be used to guide insertion of an endotracheal tube into an airway of a person. In particular, the bougie is inserted into a patient's mouth and lowered so as to enter the patient's trachea. Once the bougie has entered the trachea an airway tube can be advanced over the bougie and into a position within the trachea. The bougie can then be withdrawn through the airway tube and air can pass both directions through the airway tube. Although this discussion focuses on the bougie as used in the airway, one of skill in the art will recognize that the bougie can be used to guide various devices (e.g., chest tube, tracheal tube, cricothyrotomy tube, to name a few) into various openings in the anatomy.

Figure 4:
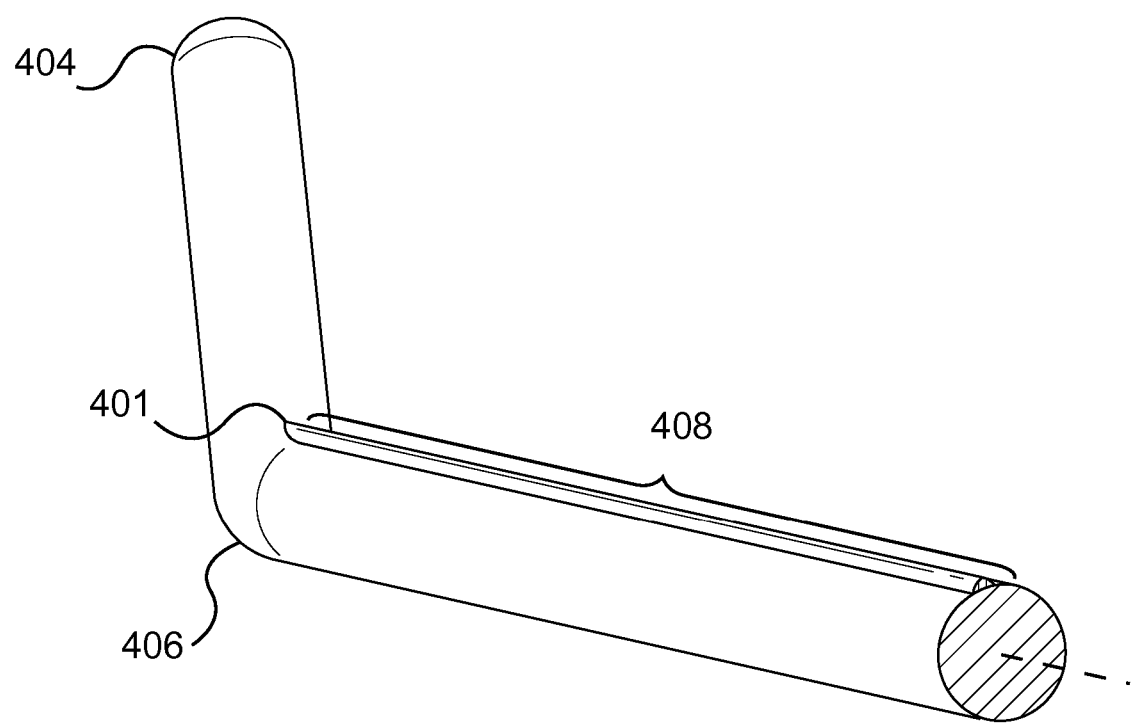
FIG. 4 illustrates a perspective view of a bougie according to another embodiment of this disclosure.

The illustrated bougie includes pairs of finger grooves 110, each pair including a finger groove on a left and a right side of the bougie. The particular illustrated embodiment shows three pairs of finger grooves 110. The finger grooves 110 can be concave and can be scalloped out of the bougie so that a user's fingers fit flush into the finger grooves 110 and can securely hold the bougie just as one would hold a pencil. Other orientations of the finger grooves 110 can be used, but in any case, their existence gives the user a tactile way to determine an axial orientation of the bougie and in particular to know which way the distal tip 104 is oriented based on a position of the user's fingers. This is particularly beneficial when the user loses sight of the bend 106. For instance, where the patient's head cannot be tilted back sufficiently to expose the trachea to view, the bougie may be bent so as to curve into the trachea thus rendering the bend 106 out of sight after a certain depth of insertion toward the trachea. In FIG. 1 the bougie is axially oriented so that the distal tip 104 is pointed upwards. The axial orientation refers to rotation of the bougie around an axis 112 passing through the main portion 108 parallel with its longest dimension. Other axial orientations might see the distal tip 104 pointed to the sides (e.g., left or right) or toward a bottom (e.g., inferior), but in each case, the main portion 108 remains in the same location as seen in FIG. 4, except rotated about the axis 112 through its longest dimension.

The finger grooves 110 can take a variety of shapes, sizes, and textures. For instance, and in addition to the scalloped shape illustrated, the finger grooves 110 could be shaped as square or rectangular grooves having an orientation perpendicular or parallel to the axis 112 through the main portion 108 parallel to its longest dimension. In some embodiments, multiple shapes can replace each groove, such that a single finger has tactile interaction with multiple concave or convex shapes rather than a single groove. For instance, a groove may comprise three protruding ridges or three concave valleys. In another example, a circular or ovular protrusion or other convex shape can replace each groove. In some instances, a combination of concave and convex shapes can be used in place of each finger groove. As seen, while finger grooves 110 have been described and illustrated, a variety of shapes and sizes of tactile indicators can be used to similar effect and these variations are easily derived by one of skill in the art without undue experimentation.

Although three pairs of finger grooves 110 are illustrated (one groove on each side), greater of fewer pairs of finger grooves 110 can be implemented. Where two or more pairs of finger grooves 110 are implemented, greater flexibility of use can be designed into the bougie since a user may desire to grip the bougie at different locations along a length of the bougie, especially where different depths of insertion are required (e.g., for patients of varying height). Where the pairs of finger grooves 110 are equally spaced from each other, they can more easily indicate different depths of insertion of the bougie. For instance, pairs of finger grooves 110 can be arranged at 10 cm, 15 cm, and 20 cm from the distal tip 104 of the bougie. In other embodiments, other distances from the distal tip 104 can be implemented. Hence, the finger grooves 110 provide both a guide to axial orientation and a guide to depth of insertion. In some embodiments, the finger grooves 110 can be colored (e.g., black) in order to provide a visual and tactile indicator of axial orientation and depth of insertion.

The bougie may have a circular cross section or any cross section that provides a tactile indication of the bougie's orientation, such as ovular or teardrop. FIG. 1 illustrates an embodiment of a circular cross section. The bougie may be made of a polymer such as aliphatic polyurethane or polytetrafluoroethylene. The bougie material can comprise a percentage of barium sulphate. Other materials that can be used for the bougie include, but are not limited to, latex, silicon, polyester, nylon, rubber, and silk. The material may be a shape memory material and may be self-lubricating.

The bougie may be a non-rigid body. In an embodiment, the bougie may be resilient within a range of deformation and beyond this range it is bendable into a shape that resumes its original shape at a rate that is typically slower than the rate of deformation.

In many cases, the bougie and/or the user's hands/gloves can become slippery due to medical fluids and patient fluids (e.g., blood, saliva, lubricants) and the bougie may become difficult to extract due to lack of friction between the bougie and the user's fingers. Thus, the proximal end 102 can include texture or other grip-enhancing mechanisms to aid a user in removing the bougie where the proximal end 102 or the main portion 108 have become slippery. For instance, the proximal end 102 can include cross-hatching formed or etched in the material in order to enhance a user's grip. This is important as to not dislodge the overriding tube, potentially causing detriment to the patient.

The bend 106 is illustrated as having a slight curve to it. However, in other embodiments, the bend may be a sharp angle or may be a longer arced region. Further, the bougie is illustrated as two straight segments connected by the bend 106. However, in other embodiments, the straight sections may have some curvature to them, and in practice the bougie may be flexible and thus depending on its use may be straight, curved, or a more complex series of multiple curves.

FIGS. 4-6 illustrate another embodiment of a bougie having a ridge 401. The bougie can include a proximal end 402 (not illustrated in FIG. 4) and a distal tip 404 and includes a bend 406 in the distal tip 404. The ridge 401 can be disposed along a superior portion of a main portion 408 of the bougie. In other embodiments, the ridge 404 can be disposed along an inferior portion of the bougie, the left or right side, or any other side of the bougie. In other embodiments, two or more ridges 401 can be implemented. For instance, a first ridge can be disposed along a superior portion and a second ridge can be disposed along an inferior portion of the main portion 408. In one embodiment, two ridges 401 can be implemented where there is a textural or structural difference between the two ridges helping to indicate an axial orientation of the bend 406. For instance, a convex ridge 401 can be disposed along a top of the bougie while a concave ridge can be disposed along a bottom of the bougie, thus providing a tactile indication as to the top and bottom of the bougie. Alternatively, a first ridge can include discontinuities, while a second ridge is continuous, thus enabling tactile distinction between a superior and an inferior side of the bougie. In some cases, a single ridge 401 also provides the same or a similar tactile indication of axial orientation.

The ridge 401 can be convex (as illustrated) or concave (not illustrated). Either way, the ridge 401 should be shaped and sized so that a user can feel the ridge through gloves and through various fluids that may be disposed on the bougie during use. The ridge 401 provides tactile indication of an axial orientation of the bougie and of the distal tip 404 when the distal tip 404 is not visible. In some embodiments, the ridge 401 can be colored (e.g., black) in order to provide a visual and tactile indicator of axial orientation and depth of insertion.

Figure 7:
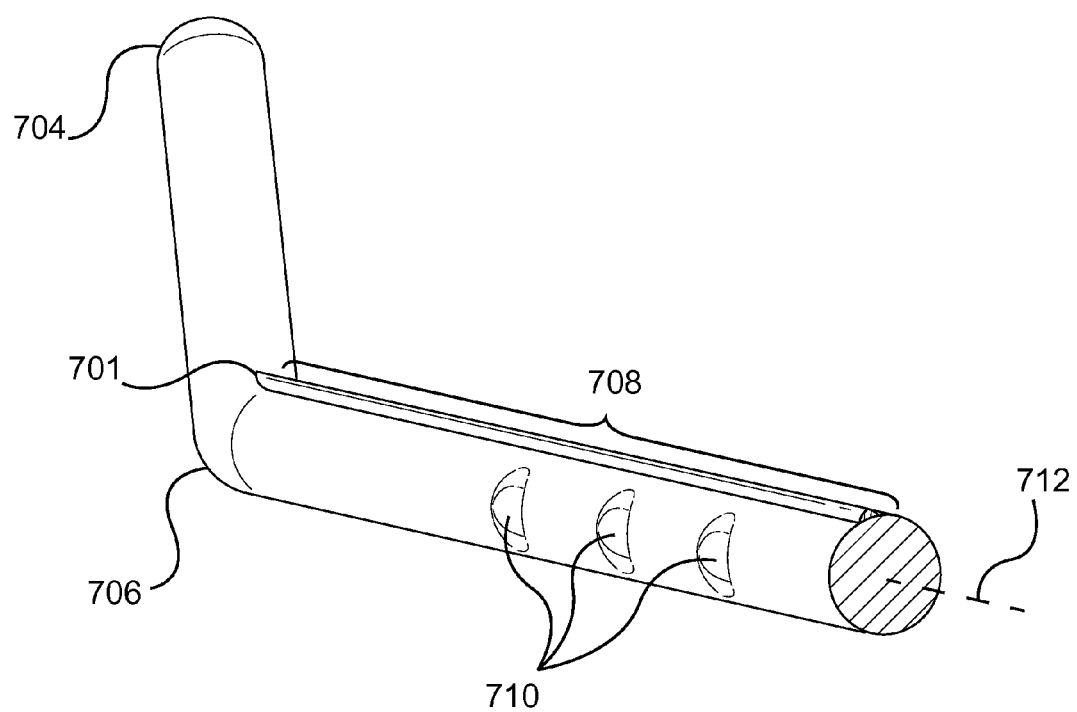
FIG. 7 illustrates a perspective view of a bougie according to yet another embodiment of this disclosure.

FIGS. 7-9 illustrate yet a further embodiment of a bougie including finger grooves 702 and a ridge 704. The bougie includes a proximal end 706 and a distal tip 708 and includes a bend 710 in the distal tip 708. The ridge 704 can be disposed along a top of the bougie. In this embodiment, both the finger grooves 702 and the ridge 704 can be used to determine an axial orientation of the bougie when the distal tip 708 is not visible. In some embodiments, one or more of the finger grooves 702 and the ridge 704 can be colored (e.g., black) in order to provide a visual and tactile indicator of axial orientation and depth of insertion.

While this disclosure has described a bougie having finger grooves and/or a ridge, one of skill in the art will recognize that any tactile indicator of bougie depth of insertion and/or axial orientation can be implemented. For instance, rather than finger grooves, convex dimples or textured patches could be used. In an embodiment, the bougie itself could have an ovular cross section so that a user could feel the thinner diameter and the thicker diameter and in this way know the axial orientation of the bougie. A teardrop cross section could also be used thus enabling tactile recognition of an axial orientation of the bougie as well as a superior side of the bougie as distinguished from its inferior side.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A bougie comprising:
   a flexible elongated distal portion; and
   a flexible elongated main portion coupled to the distal portion, a longitudinal axis of the distal portion being at an angle relative to a longitudinal axis of the main portion, the main portion being longer than the distal portion, the angle oriented toward a superior side of the main portion,
   the main portion including one or more pairs of concave finger grooves, each pair including a finger groove on a left side and on a right side of the main portion, a distance between each pair bisected by the ridge, the finger grooves providing a tactile indication of an axial orientation of the bougie, providing a tactile indication of a depth of insertion of the bougie into a patient's trachea, and providing improved grip when the bougie becomes slippery due to blood, secretions, or other liquids, the main portion further comprising a ridge running along at least a majority of a superior portion of the main portion and parallel to the longitudinal axis of the main portion.

2. The bougie of claim 1, wherein there is one pair of finger grooves.

3. The bougie of claim 1, wherein there are two or more pairs of finger grooves.

4. The bougie of claim 3, wherein each of the two or more pairs of finger grooves are equally spaced from each other along a length of the main portion so as to provide a tactile indication of the depth of insertion.

5. The bougie of claim 1, wherein the ridge protrudes from a circular or elliptical cross section of the main portion along a plane that intersects and is parallel to the longitudinal axis of the flexible elongated distal portion.

6. The bougie of claim 1, wherein the ridge extends radially out from the main portion a radial distance that is less than half a diameter of a cross section of the main portion.

7. The bougie of claim 6, wherein the ridge extends radially out from the main portion, and the main portion has substantially the same flexibility in all axes.

8. The bougie of claim 1, wherein the ridge is continuous.

9. The bougie of claim 1, wherein the ridge is discontinuous.

10. A bougie comprising:
a flexible elongated main portion;
a ridge running along a superior side of the flexible elongated main portion parallel to a longitudinal axis of the flexible elongated main portion and arranged to provide a tactile indication of an axial orientation of the bougie, the ridge being recognizable to human touch even when obscured to view, the ridge further providing improved grip when the bougie becomes slippery due to blood, secretions, or other liquids; and
the main portion having one or more pairs of finger grooves, each pair of finger grooves having a distance therebetween bisected by the ridge.

11. The bougie of claim 10, further comprising a flexible elongated distal portion coupled to the flexible elongated main portion, a longitudinal axis of the distal portion being at an angle relative to a longitudinal axis of the main portion, the main portion, wherein the flexible elongated main portion is longer than the flexible elongated distal portion, the angle oriented toward the superior side of the flexible elongated main portion.

12. The bougie of claim 10, wherein the ridge is arranged along an entire superior portion of the flexible elongated main portion.

13. The bougie of claim 10, further comprising one or more raised features along a left and a right side of the flexible elongated main portion of the bougie.

14. The bougie of claim 10, further comprising two pairs of finger grooves.

15. The bougie of claim 14, wherein each of the two sets of finger grooves includes a row of finger grooves running parallel to a longitudinal axis of the main portion and where the finger grooves in each row are equally spaced along a length of the bougie so as to provide another tactile indication of the depth of insertion.

16. The bougie of claim 10, wherein a proximal end of the bougie includes texture to aid in removal of the bougie from a patient's airway.

17. The bougie of claim 10, wherein the ridge is continuous.

18. The bougie of claim 10, wherein the ridge is discontinuous.

19. A method comprising:
providing a bougie having an elongate shape, a bent distal tip, and one or more tactile indicators of an orientation of the bent distal tip and a depth of insertion of the bougie, the one or more tactile indicators providing improved grip when the bougie becomes slippery due to blood, secretions, or other liquids, the one or more tactile indicators including at least: (1) a ridge running along at least a portion of a superior portion of the bougie, and (2) one or more pairs of finger grooves along a left and right side of the ridge, a distance between each pair bisected by the ridge;
rotating the bougie until the one or more tactile indicators indicates that the distal tip of the bougie is pointed toward an anterior side of the trachea; and
moving the bougie into a patient, at least some of the ridge passing through a glottic opening of the patient, until the one or more tactile indicators indicates that the bougie has entered the trachea.

20. The bougie of claim 19, wherein the ridge is continuous.

21. The bougie of claim 19, wherein the ridge is discontinuous.

* * * * *